(12) United States Patent
Xu et al.

(10) Patent No.: US 9,365,488 B2
(45) Date of Patent: Jun. 14, 2016

(54) SAFE METHOD FOR PRODUCING ALKYL NITRATE

(71) Applicant: SHANDONG LIBAODE CHEMICAL CO., LTD., Heze (CN)

(72) Inventors: Deliang Xu, Heze (CN); Hengtao Mao, Heze (CN)

(73) Assignee: SHANDONG LIBAODE CHEMICAL CO., LTD., Heze (CN)

( * ) Notice: Subject to any disclaimer, the term of this patent is extended or adjusted under 35 U.S.C. 154(b) by 0 days.

(21) Appl. No.: 14/374,031

(22) PCT Filed: Dec. 21, 2012

(86) PCT No.: PCT/CN2012/087148
§ 371 (c)(1),
(2) Date: Jul. 23, 2014

(87) PCT Pub. No.: WO2014/086065
PCT Pub. Date: Jun. 12, 2014

(65) Prior Publication Data
US 2015/0031909 A1 Jan. 29, 2015

(30) Foreign Application Priority Data

Dec. 4, 2012 (CN) .......................... 2012 1 0514448

(51) Int. Cl.
| C07C 201/02 | (2006.01) |
| C07C 203/04 | (2006.01) |
| C07C 203/08 | (2006.01) |

(52) U.S. Cl.
CPC .................................... C07C 201/02 (2013.01)

(58) Field of Classification Search
CPC .... C07C 201/02; C07C 203/04; C07C 230/08
See application file for complete search history.

(56) References Cited

U.S. PATENT DOCUMENTS

| 2,254,352 | A | * | 9/1941 | Cloud | C07C 201/02 |
| | | | | | 210/205 |
| 2,618,650 | A | * | 11/1952 | Hinkamp | C07C 201/02 |
| | | | | | 558/480 |
| 2,768,964 | A | * | 10/1956 | Spaeth | C07C 201/02 |
| | | | | | 558/480 |
| 2,840,303 | A | | 6/1958 | Stuart | |
| 4,479,905 | A | | 10/1984 | Knapp et al. | |
| 7,947,855 | B2 | * | 5/2011 | Scubla | C07C 203/04 |
| | | | | | 558/483 |

FOREIGN PATENT DOCUMENTS

| CN | 1031525 | 3/1989 | |
| CN | 1045773 | 10/1990 | |
| CN | 200977420 | 11/2007 | |
| CN | 101462962 | 6/2009 | |
| CN | 101698646 | 4/2010 | |
| CN | 201949682 | 8/2011 | |
| CN | 102557953 | 7/2012 | |
| GB | 731438 A | * 6/1955 | ............ C07C 203/04 |
| GB | 808294 A | * 2/1959 | ............ C07C 201/02 |
| GB | 832870 A | * 4/1960 | ............ C07C 201/02 |
| RU | 2259348 | 8/2005 | |
| RU | 91717 | 2/2010 | |

OTHER PUBLICATIONS

International search report of PCT/CN2012/087148, dated Sep. 12, 2013 (6 pages total).

* cited by examiner

*Primary Examiner* — Nyeemah A Grazier
(74) *Attorney, Agent, or Firm* — Hamre, Schumann, Mueller & Larson, P.C.

(57) ABSTRACT

The present invention provides a method for producing alkyl nitrate. The centrifugal extraction equipment acts as the esterification separator; a mixed acid solution containing sulfuric acid and nitric acid enters from the heavy phase inlet of the centrifugal extraction equipment; alkyl alcohol enters from the light phase inlet of the centrifugal extraction equipment; the feeding molar ratio of alkyl alcohol and nitric acid equals to 1:1.0-3.0; esterification reaction occurs with the mixed acid and alkyl alcohol at a temperature of 10~60° C. under the rotating speed of 800-2000 r/min; under the action of centrifugal force, the generated coarse ester as a light phase and the spent acid as a heavy phase are separated; coarse ester as a light phase is discharged through the light-phase outlet of the centrifugal extractor; the spent acid as a heavy phase is discharged through the heavy-phase outlet of the centrifugal extractor; after alkali washing and water washing conventionally, coarse ester is dehydrated for drying and purified, then the refining products of alkyl nitrate is obtained. In the method of the present invention, esterification reaction, the separation of reaction products and the spent acid are finished in the same reactor simultaneously, which reduces the contact time of reaction products with the spent acid greatly, avoids the side reaction effectively, and ensures the safety of esterification process.

10 Claims, 1 Drawing Sheet

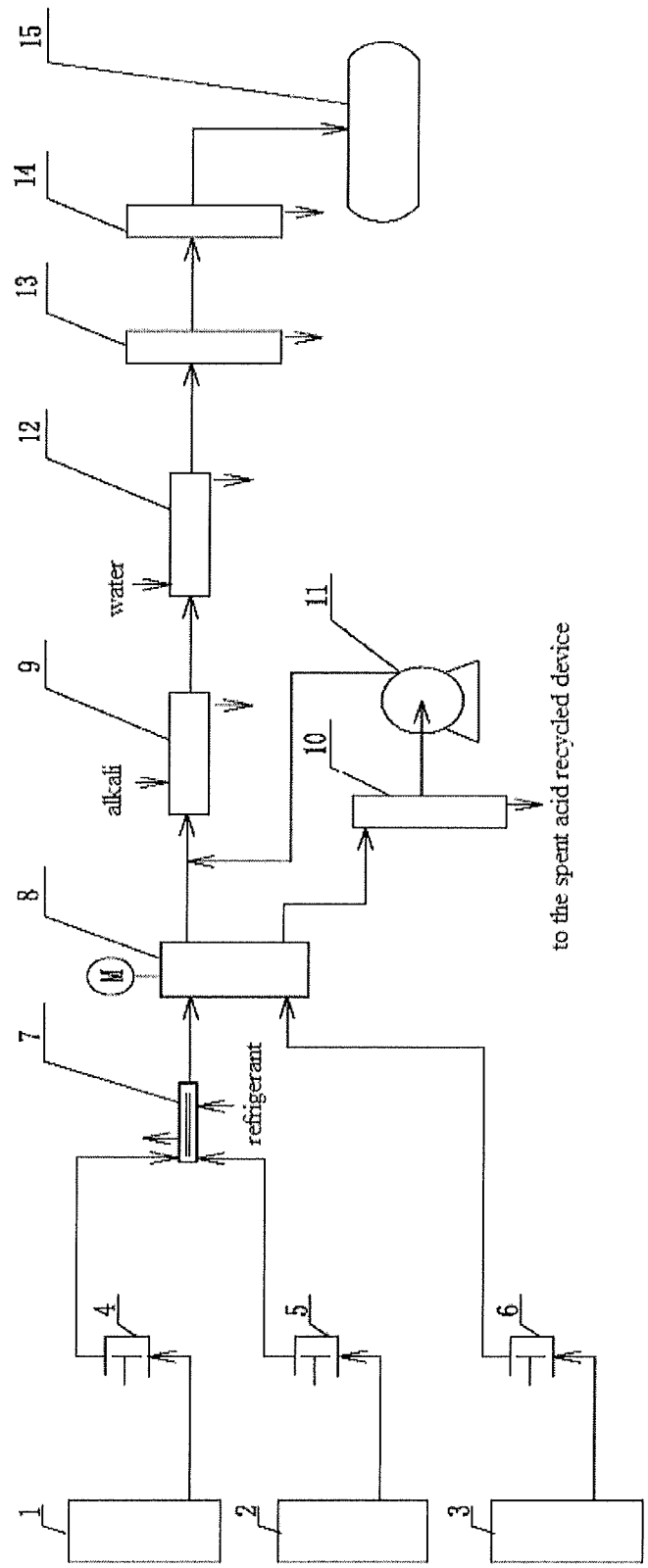

SAFE METHOD FOR PRODUCING ALKYL NITRATE

FIELD OF THE INVENTION

The present application relates to the technical field of synthesizing alkyl nitrate compounds from the esterification (or nitrification) reaction of alkyl alcohol compounds with nitric acid under the action of acidic catalysts, particularly to a method for producing alkyl nitrate.

BACKGROUND OF THE INVENTION

The mixed-acid method is generally used in the production of isooctyl nitrate traditionally, i.e., at room temperature or low temperature condition, isooctyl alcohol is added drop-wise to the mixture of acid consist of nitric acid and sulfuric acid. To maintain the low temperature of reaction system, the refrigerating brine is used to remove the heat generated by the esterification reaction. After the reaction finished, the product is poured into cold water for stratification, then the layer of ester is washed. Throughout the process, in order to prevent the side reactions of branched oxidation and nitrosation, all the operations must be carried out at low temperature, and a refrigerating machine must be needed to keep a steady low-temperature operation continuously. The investment of these devices and their ancillary equipments is large and energy consumption is also high. U.S. Pat. No. 2,768,964 (1956) provided a method for producing water and ester by azeotropical distillation under reduced pressure, through which nitrate of low boiling point was obtained with higher yield, but, the yield was only about 50% for nitrate of high boiling point; U.S. Pat. No. 4,479,905 (1984) provided a method for nitrifying the mixture of ethoxyethanol and isooctanol continuously. Thereof, at low temperature, the mixed acid ratio of water:nitric acid:sulfuric acid equaled to 12:20:68; Chinese Patent CN1031525A (1989) presented that at below 40° C. (optimum conditions: below 25° C. the mixed acid ratio of water:nitric acid:sulfuric acid equaled to 7-13:20-25:62-68, and the yield was 95-97%; Chinese patent ZL90105260.4 provided a method that at the temperature of 50-75° C., the mixed acid ratio of water:nitric acid:sulfuric acid equaled to 22-30:13-48:28-61, urea with 1-6% by weight of the mixed acid was added as stabilizer, blankets or other lipophilic hydrophobic materials were used for physical dehydration.

As to above technologies, some need cold source produced by refrigeration devices to keep reaction conditions at a low temperature, and the reaction is intermittent reaction. Because the reaction is exothermic process, the heat should be removed continuously to maintain the low temperature conditions of the system; when failure leads to disruption of refrigerant supply, the rising reaction temperature of the system promotes side reaction, consequently, the side reaction will release more heat so that the temperature of the system will rise rapidly, and eventually side reactions and oxidation reaction become main reactions. At this time, not only materials are lost largely, but also accidents such as material spraying or explosion are prone to occur, which endanger the safety of personnel and equipments, and will pollute the environment. The disadvantages of azeotropic distillation are high energy consumption and the problems of fundamental guarantee production safety. Although Chinese Patent ZL90105260.4 used overflow series reactor, but the equipments and processes were complex, the operation was difficult, more materials were stored in the system and there were still a lot of security risks.

In addition, the Chinese patent CN101698646A and CN101462962A also provided the process of producing isooctyl nitrate, which used a micro-tube (channel) reactor, but it was still unable to separate products in a timely manner. And because the channels of micro-tube (channel) reactor were much thin, which could easily be clogged by solid impurities from raw materials then the process was forced to shut down, so there were some limitations for the micro-tube (channel) reactor.

According to all of the above technologies, there exists a common security risk that the reaction product (ester) and the waste acid formed after the reaction can not be separated timely. The product may be further oxidized, which not only affects the quality and safety of the product, but also threats seriously to the safety of equipments and personnel.

SUMMARY OF THE INVENTION

The object of the present invention is to provide a process of esterification (or nitrification) reaction, and the reaction products with the waste acid formed in the reaction are separated in the same reactor simultaneously, assisted by DCS to implement the automatic process of continuous production and continuous dehydration.

The above object of the present invention is achieved through the following technical solutions:

A method for producing alkyl nitrate, comprising the steps of:

1) The centrifugal extraction equipment acts as the esterification separator; a mixed acid solution containing sulfuric acid and nitric acid enters from the heavy phase inlet of the centrifugal extraction equipment; alkyl alcohol enters from the light phase inlet of the centrifugal extraction equipment; the feeding molar ratio of alkyl alcohol and nitric acid equals to 1:1.0-3.0; esterification reaction occurs with the mixed acid and alkyl alcohol at a temperature of 10~60° C. and at the rotating speed of 800-2000 r/min;

2) under the action of centrifugal force, coarse ester produced from the esterification reaction of Step 1) as a light phase and the remaining spent acid after reaction as a heavy phase are separated; coarse ester as a light phase is discharged through the light-phase outlet of the centrifugal extractor; the spent acid as a heavy phase is discharged through the heavy-phase outlet of the centrifugal extractor; after alkali washing and water washing conventionally, coarse ester is dehydrated for drying and purified, then the refined products of alkyl nitrate are obtained.

In the method of the present invention, in the step 1), wherein the alcohol is preferably C3-C9 alkyl alcohol; more preferably isooctyl alcohol, isoamyl alcohol, cyclohexanol or isopropanol.

In the method of the present invention, in the step 1), wherein the mixed acid solution contains preferably 30-80% sulfuric acid and nitric acid of 10-40% by weight; and more preferably 40-78% sulfuric acid and 10-35% nitric acid; and water for the rest.

In the method of the present invention, in the step 1), wherein the feeding molar ratio of alcohol and nitric acid is preferably 1:1.0-2.0.

In the method of the present invention, in the step 1), wherein the reaction temperature is preferably 15-50° C.

In the method of the present invention, in the step 1), wherein the rotating speed of centrifugal extraction equipment is preferably 1200-1500 r/min.

In the method of the present invention, wherein the centrifugal extraction equipment can be various commercial centrifugal extraction separators, centrifugal extractors or other mechanical equipments which are referred to as "centrifugal extraction separation apparatus" by the person skilled in the art, such as HL-125 centrifugal extractor developed by the Institute of Beijing Extraction Application Technology, U.S. CINC V2 multi-function centrifugal separation extractors, centrifugal extraction equipments disclosed by Chinese patent literature CN201949682U, CN200977420Y, and so on.

In the method of the present invention, in the step 2), wherein the coalescence dehydrator is preferably used for dehydration, with which water and insoluble materials in coarse ester can be removed by filtration.

The coalescence dehydrator described above can be selected from various coalescence dehydrators with the same principles in the prior art. The products are dehydrated for drying by the coalescence dehydrator with the principle of coalescence separation. When coarse ester flows through the coalescence dehydrator, the tiny water droplets which emulsified in the coarse ester aggregate for growing by the internal coalescence layer, then they are sedimentated in the bottom of the device. The filter core for separation make organic materials outflow smoothly from the device and prevent water droplets through. Finally the purpose of dewatering is achieved.

In the method of the present invention, in the step 2), wherein the spent acid outflowing from the centrifugal extraction equipment can be partially returned to the preparation step of the mixed acid as raw materials for preparing the mixed acid again, and the excess part enters into the spent acid storage tank.

Compared with the traditional process using tank reactor and micro-tube reactor in the prior art, the present invention has following advantages:

1. In the method of the present invention, the centrifugal extraction equipment is selected as the esterification separator; because of its unique structure and centrifugal force, esterification reaction can be completed instantly, and the spent acid after the reaction and ester as target reaction product can be separated rapidly and effectively; in the whole process, the short contact time of materials and full reaction, avoid the oxidation side reaction and decomposition reaction of products because of long-time contacting, ensure the quality of products and improve the yield.

2. Compared with the traditional tank reactor, the centrifugal extractor is selected as the reactor in the present invention, which reduces the size of the reactor greatly. In the same capacity, the internal material volume in the reactor is only 0.6-1% of the material volume compared to traditional reactor. The smaller amount of material volume decreasess the risk degree of the reaction system greatly and the materials of the system can be drained rapidly in the event of sudden failure (such as cutting off the electricity, cutting off the water, other equipment failures) to prevent the occurrence of the safety accidents such as materials spraying or explosion.

3. Compared with the micro-tube reactor, the centrifugal extractor as the reactor in the present invention can make the reaction materials mix more quickly and fully, and then make the esterification reaction occur more rapidly and adequately. Under the condition of so rapid and adequate reaction, the requirement of the reaction for the impurities content of raw materials is lower, it is not prone to block the internal reactor even if in the long-time production, the reaction and separation can be completed in the same equipment, and cost and loss of production are lower.

4. In the present invention, the centrifugal extractor as the reactor shortens the startup time and shutdown time of production, so it is not only reduce the quantity of materials for processing and postprocessing, but also reduce the fluctuation of the process during startup and shutdown period, thereby decreases the risk of quality and safety.

5. The method of the present invention can achieve the automatic control and reduce staffing.

6. In the present invention, the centrifugal extractor as the reactor increases the control range of reaction equipment and the capacity of production can be adjusted randomly between 20-100%.

7. In the preferred embodiments, by the coalescence separator for dehydration, good effect and high efficiency are achieved, by which the consumption of using desiccants and adsorption loss of products in the desiccants are avoided, the quality of products is stable, and the yield of products is improved.

DESCRIPTION OF FIGURE

FIG. 1 is a schematic diagram of the method for producing alkyl nitrate in the present invention.

In the FIG. 1: 1 for sulfuric acid tank, 2 for nitric acid tank, 3 for octanol tank, 4 for metering pump of sulfuric acid, 5 for metering pump of nitric acid, 6 for metering pump of octanol, 7 for jacketed static mixer, 8 for separator of esterification reaction, 9 for alkali washing device, 10 for oil-water separator, 11 for centrifugal pump, 12 for water washing device, 13 for oil-water separator, 14 for coalescence dehydrator, 15 for storage tank of products.

EXAMPLES

The technical scheme of the present invention can be carried in accordance with the following specific implementation:

As shown in FIG. 1, a certain proportion of sulfuric acid and nitric acid from the sulfuric acid tank 1 and the nitric acid tank 2 flow into the heat transfer jacketed static mixer 7 respectively by each metering pump to be mixed fully, then enter into the separator of esterification reaction 8 from different feed inlets with precisely metered alkyl alcohol from the octanol tank 3 (where, the conventional centrifugal extraction equipment acts as the esterification separator; a mixed acid enters from its inlet of heavy phase; alcohol enters from its inlet of light phase), these materials react adequately under the action of centrifugal force, and the ester and spent acid after reaction are separated fast, they flow out of the separator of esterification reaction 8 from the respective outlets (where, the conventional centrifugal extraction equipment acts as the esterification separator; spent acid solution flows out from its outlet of heavy phase; ester flows out from its outlet of light phase). The outflow of coarse ester with a small amount of spent acid (the amount for entrainment can be adjusted by changing the strength of centrifugal force), are completely separated by the oil-water separator 10, the part of spent sulfuric acid returns to the preparation process of mixed acid as raw materials to prepare mixed acid again and the excess part flows into the spent acid storage tank; the coarse ester is further processed throughout the alkali washing device 9, the water washing device 12, the oil-water separator 13 then into the coalescence dehydrator 14, in which water and insoluble materials entrained in coarse ester are filtered and removed, and the purified products after testing qualified enter into the storage tank of products 15.

Example 1

The Method for Producing Isooctyl Nitrate

Detailed steps including:

1) HL-125 centrifugal extractor developed by the Institute of Beijing Extraction Application Technology acts as the esterification separator; the mixed acid solution according to the water:nitric acid:sulfuric acid=15:25:60 by weight enters from the heavy phase inlet of the centrifugal extractor; isooctyl alcohol enters from the light phase inlet of the centrifugal extractor; the mixed acid solution and isooctyl alcohol are sent to the centrifugal extractor continuously by the metering pump at the same time, wherein the feeding molar ratio of isooctyl alcohol and nitric acid equaling to 1:1.5; esterification reaction occurs with the mixed acid and alcohol at a temperature of 40~50° C.; and at the rotating speed of 1100 r/min;

2) under the action of centrifugal force, coarse ester produced from the esterification reaction of Step 1) as a light phase and the remaining spent acid after reaction as a heavy phase are separated in the inner of the reactor; coarse ester as a light phase is discharged through the light-phase outlet of the centrifugal extractor; the spent acid as a heavy phase is discharged through the heavy-phase outlet of the centrifugal extractor;

3) the part of spent acid flowing from the centrifugal extractor in step 2) returns to the preparation process of mixed acid to be recycled and the other part flows into the spent acid storage tank; after alkali washing and water washing conventionally, coarse ester discharged from the centrifugal extractor in step 2) enters into the coalescence dehydrator, in which coarse ester is treated by the filter cores of coalescence and separation, and the dehydrated water is removed from the bottom of the coalescence dehydrator regularly. The refined ester after dehydration is discharged from the coalescence dehydrator, then it enters into the storage tank of products after testing qualified.

The purity of obtained isooctyl nitrate by the present example is 99.5%, and the yield is 99%. When the effective volume of the esterification separator is 20 L, the production of isooctyl nitrate is 50-300 kg/h continuously adjustable.

Example 2

The Method for Producing Isooctyl Nitrate

The process is the same as the Example 1. The ratio of mixing acid for water:nitric acid:sulfuric acid is changed to 18:20:62, the purity of the product is 99.4% and the yield is 98.8%.

Example 3

The Method for Producing Isooctyl Nitrate

The process is the same as the Example 1. The ratio of alcohol:nitrate acid is changed to 1:1.8 (mole ratio), the purity of the product is 99.3% and the yield is 99%.

Example 4

The Method for Producing Isopropyl Nitrate

1) HL-50 centrifugal extractor developed by the Institute of Beijing Extraction Application Technology acts as the esterification separator; the mixed acid solution according to the water:nitric acid:sulfuric acid=15:30:55 by weight enters from the heavy phase inlet of the centrifugal extractor; isopropyl alcohol enters from the light phase inlet of the centrifugal extractor; the mixed acid solution and isopropyl alcohol are sent to the centrifugal extractor continuously by the metering pump at the same time, wherein the feeding molar ratio of isopropyl alcohol and nitric acid equaling to 1:1.9; esterification reaction occurs with the mixed acid and isopropyl alcohol at a temperature of 10-35° C. and at the rotating speed of 1200 r/min;

2) under the action of centrifugal force, coarse isopropyl nitrate produced from the esterification reaction of Step 1) as a light phase and the remaining spent acid after reaction as a heavy phase are separated in the inner of the reactor; coarse ester as a light phase is discharged through the light-phase outlet of the centrifugal extractor; the spent acid as a heavy phase is discharged through the heavy-phase outlet of the centrifugal extractor;

3) the part of spent acid flowing from the centrifugal extractor in step 2) returns to the preparation process of mixed acid to be recycled and the other part flows into the spent acid storage tank; after alkali washing and water washing conventionally, coarse ester discharged from the centrifugal extractor in step 2) enters into the coalescence dehydrator, in which coarse ester is treated by the filter cores of coalescence and separation, and the water dehydrated is removed from the bottom of the coalescence dehydrator regularly. The refined ester after dehydration is discharged from the coalescence dehydrator, then it enters into the storage tank of products after testing qualified.

The purity of obtained isopropyl nitrate by the present example is 99.5%, and the yield is 96%.

Example 5

The Method for Producing Isoamyl Nitrate

1) HL-50 centrifugal extractor developed by the Institute of Beijing Extraction Application Technology acts as the esterification separator; the mixed acid solution according to the water:nitric acid:sulfuric acid=26:25:49 by weight enters from the heavy phase inlet of the centrifugal extractor; isoamyl alcohol enters from the light phase inlet of the centrifugal extractor; the mixed acid solution and isoamyl alcohol are sent to the centrifugal extractor continuously by the metering pump at the same time, wherein the feeding molar ratio of isoamyl alcohol and nitric acid equaling to 1:2.2; esterification reaction occurs with the mixed acid and isoamyl alcohol at a temperature of 25-40° C. and at the rotating speed of 1000 r/min;

2) under the action of centrifugal force, coarse isopropyl nitrate produced from the esterification reaction of Step 1) as a light phase and the remaining spent acid after reaction as a heavy phase are separated in the inner of the reactor; coarse ester as a light phase is discharged through the light-phase outlet of the centrifugal extractor; the spent acid as a heavy phase is discharged through the heavy-phase outlet of the centrifugal extractor;

3) the part of spent acid flowing from the centrifugal extractor in step 2) returns to the preparation process of mixed acid to be recycled and the other part flows into the spent acid storage tank; after alkali washing and water washing conventionally, coarse ester discharged from the centrifugal extractor in step 2) enters into the coalescence dehydrator, in which coarse ester is treated by the filter cores of coalescence and separation, and the water dehydrated is removed from the bottom of the coalescence dehydrator regularly. The refined ester after dehydration is discharged from the coalescence dehydrator, then it enters into the storage tank of products after testing qualified.

The purity of obtained isoamyl nitrate by the present example is 99.6%, and the yield is 97%.

We claim:

1. A method for producing alkyl nitrate comprising:
   1) conducting an esterification reaction to obtain a coarse ester of alkyl nitrate in a centrifugal extraction equipment, wherein the centrifugal extraction equipment has a heavy phase inlet and a light phase inlet; a mixed acid solution containing sulfuric acid and nitric acid enters the centrifugal extraction equipment from the heavy phase inlet; alkyl alcohol enters the centrifugal extraction equipment from the light phase inlet; a feeding molar ratio of alkyl alcohol and nitric acid equals to 1:1.0-3.0; the esterification reaction is conducted at a temperature of 10~60 ° C. and at a rotating speed of 800-2000 r/min;
   2) separating the coarse ester of alkyl nitrate from spent acid in the centrifugal extraction equipment, wherein the centrifugal extraction equipment further contains a heavy phase outlet and a light phase outlet; under the action of centrifugal force, the coarse ester produced from the esterification reaction forms a light phase and the spent acid after reaction forms a heavy phase; the coarse ester as a light phase is discharged from the centrifugal extraction equipment through the light-phase outlet; the spent acid as a heavy phase is discharged from the centrifugal extraction equipment through the heavy-phase outlet;
   3) refining and dehydrating the coarse ester discharged from the centrifugal extraction equipment to obtain purified alkyl nitrate, wherein the coarse ester undergoes a process including alkali washing, water washing, and dehydration;

wherein the centrifugal extraction equipment acts as both a reactor for the esterification reaction and a separator for isolating the coarse ester of alkyl nitrate from spent acid.

2. The method of claim 1, wherein the alkyl alcohol is C3-C9 low-carbon alcohol.

3. The method of claim 2, wherein the C3-C9 low-carbon alcohol is isooctyl alcohol, isoamyl alcohol, isopropanol or cyclohexanol.

4. The method of claim 1, wherein the mixed acid solution contains 30-80% sulfuric acid and nitric acid of 10-40% by weight, and water for the rest.

5. The method of claim 1, wherein the mixed acid solution contains 40-78% sulfuric acid and nitric acid of 10-35% by weight, and water for the rest.

6. The method of claim 1, wherein the feeding molar ratio of alcohol and nitric acid is 1:1.0-2.0.

7. The method of claim 1, wherein the reaction temperature is 15-50° C.

8. The method of claim 1, wherein the rotating speed of centrifugal extraction equipment is 1200-1500 r/min.

9. The method of claim 1, wherein a coalescence dehydrator is used for the process of the dehydration.

10. The method of claim 1, wherein the spent acid discharged from the centrifugal extraction equipment can be partially returned to a preparation step of the mixed acid as raw materials for preparing the mixed acid again, and an excess enters into a spent acid storage tank.

* * * * *